US007650628B2

(12) United States Patent  
Zimmerman et al.

(10) Patent No.: US 7,650,628 B2  
(45) Date of Patent: Jan. 19, 2010

(54) TRANSCRIPTION DATA SECURITY

(75) Inventors: Roger S. Zimmerman, Wellesley, MA (US); Paul Egerman, Weston, MA (US); Benjamin Chigier, Wellesley, MA (US)

(73) Assignee: eScription, Inc., Needham, MA (US)

( * ) Notice: Subject to any disclaimer, the term of this patent is extended or adjusted under 35 U.S.C. 154(b) by 655 days.

(21) Appl. No.: 10/970,617

(22) Filed: Oct. 21, 2004

(65) Prior Publication Data

US 2006/0089857 A1    Apr. 27, 2006

(51) Int. Cl.
*G06F 7/04* (2006.01)
*G06F 17/30* (2006.01)
*H04L 9/32* (2006.01)

(52) U.S. Cl. .......................................... 726/2; 380/277
(58) Field of Classification Search ...................... 726/2, 726/26; 713/200, 17; 704/270, 238, 240; 380/277
See application file for complete search history.

(56) References Cited

U.S. PATENT DOCUMENTS

| | | | | |
|---|---|---|---|---|
| 5,146,439 | A | 9/1992 | Jachmann et al. | 369/25 |
| 5,519,808 | A | 5/1996 | Benton, Jr. et al. | 395/2.79 |
| 5,602,982 | A | 2/1997 | Judd et al. | 395/326 |
| 5,748,888 | A * | 5/1998 | Angelo et al. | 726/26 |
| 5,812,882 | A | 9/1998 | Raji et al. | 395/892 |
| 5,857,212 | A | 1/1999 | Van De Vanter | 707/519 |
| 5,875,448 | A | 2/1999 | Boys et al. | 707/531 |
| 6,374,225 | B1 | 4/2002 | Hejna, Jr. | 704/270 |
| 6,415,256 | B1 | 7/2002 | Ditzik | 704/231 |
| 6,438,545 | B1 | 8/2002 | Beauregard et al. | 707/6 |
| 6,865,258 | B1 | 3/2005 | Polcyn | 379/88.01 |
| 6,950,994 | B2 | 9/2005 | Dharap | 715/864 |
| 6,961,699 | B1 | 11/2005 | Kahn et al. | 704/235 |
| 6,996,445 | B1 | 2/2006 | Kamijo | 700/94 |
| 7,016,844 | B2 * | 3/2006 | Othmer et al. | 704/270.1 |
| 7,236,932 | B1 | 6/2007 | Grajski | 704/277 |
| 2003/0046080 | A1 | 3/2003 | Hejna, Jr. | 704/270 |
| 2003/0067495 | A1 | 4/2003 | Pu et al. | 345/811 |
| 2005/0149747 | A1 * | 7/2005 | Wesinger et al. | 713/200 |
| 2006/0075243 | A1 * | 4/2006 | Lakamp et al. | 713/176 |
| 2006/0206943 | A1 * | 9/2006 | Ellison et al. | 726/26 |
| 2006/0253895 | A1 * | 11/2006 | Brandofino et al. | 726/2 |
| 2006/0272025 | A1 * | 11/2006 | Mononen | 726/26 |
| 2007/0118751 | A1 * | 5/2007 | Parlett et al. | 713/176 |
| 2007/0136058 | A1 * | 6/2007 | Jeong et al. | 704/240 |
| 2007/0143857 | A1 * | 6/2007 | Ansari | 726/26 |

(Continued)

OTHER PUBLICATIONS

Batty, S.V.; Garner, P.E.; Howard, D.M.; Turner, P.; White, A.D., The development of a portable real-time display of voice source characteristics, vol. 2, Oct. 25-28, 2001 pp. 1449-1452.*

(Continued)

*Primary Examiner*—Kambiz Zand
*Assistant Examiner*—Monjour Rahim
(74) *Attorney, Agent, or Firm*—Wolf, Greenfield & Sacks, P.C.

(57) ABSTRACT

A computer program product for use with dictated medical patient information resides on a computer-readable medium and comprises computer-readable instructions for causing a computer to analyze the dictated information, identify likely confidential information in the dictated medical patient information, and treat the likely confidential information disparately from likely non-confidential information in the dictated medical patient information.

18 Claims, 6 Drawing Sheets

U.S. PATENT DOCUMENTS

| | | | |
|---|---|---|---|
| 2007/0185712 A1* | 8/2007 | Jeong et al. | 704/238 |
| 2007/0225980 A1* | 9/2007 | Sumita | 704/240 |
| 2007/0225981 A1* | 9/2007 | Kim | 704/240 |
| 2007/0256139 A1* | 11/2007 | Gaos et al. | 726/26 |
| 2007/0266252 A1* | 11/2007 | Davis et al. | 713/176 |
| 2007/0283444 A1* | 12/2007 | Jang | 726/26 |
| 2007/0294745 A1* | 12/2007 | Tan et al. | 726/2 |
| 2007/0300287 A1* | 12/2007 | Wynne et al. | 726/2 |
| 2008/0022113 A1* | 1/2008 | Moskowitz | 713/176 |
| 2008/0059174 A1* | 3/2008 | Hershey et al. | 704/240 |
| 2008/0059799 A1* | 3/2008 | Scarlata | 713/176 |

OTHER PUBLICATIONS

Batty et al., "The development of a portable real-time display of voice source characteristics", *IEEE*, 2:419-422 (2000).

* cited by examiner

TRANSCRIPTION DATA SECURITY

BACKGROUND OF THE INVENTION

Healthcare costs in the United States account for a significant share of the GNP. The affordability of healthcare is of great concern to many Americans. Technological innovations offer an important leverage to reduce healthcare costs.

Many Healthcare institutions require doctors to keep accurate and detailed records concerning diagnosis and treatment of patients. Motivation for keeping such records include government regulations (such as Medicare and Medicaid regulations), desire for the best outcome for the patient, and mitigation of liability. The records include patient notes that reflect information that a doctor or other person adds to a patient record after a given diagnosis, patient interaction, lab test or the like.

Record keeping can be a time-consuming task, and the physician's time is valuable. The time required for a physician to hand-write or type patient notes can represent a significant expense. Verbal dictation of patient notes offers significant time savings to physicians, and is becoming increasingly prevalent in modern healthcare organizations.

Over time, a significant industry has evolved around the transcription of medical dictation. Several companies produce special-purpose voice mailbox systems for storing medical dictation. These centralized systems hold voice mailboxes for a large number of physicians, each of whom can access a voice mailbox by dialing a phone number and putting in his or her identification code. These dictation voice mailbox systems are typically purchased or shared by healthcare institutions. Prices can be over $100,000 per voice mailbox system. Even at these prices, these centralized systems save healthcare institutions vast sums of money over the cost of maintaining records in a more distributed fashion.

Using today's voice mailbox medical dictation systems, when a doctor completes an interaction with a patient, the doctor calls a dictation voice mailbox, and dictates the records of the interaction with the patient. The voice mailbox is later accessed by a medical transcriptionist who listens to the audio and transcribes the audio into a text record. The playback of the audio data from the voice mailbox may be controlled by the transcriptionist through a set of foot pedals that mimic the action of the "forward", "play", and "rewind" buttons on a tape player. Should a transcriptionist hear an unfamiliar word, the standard practice is to stop the audio playback and look up the word in a printed dictionary.

The medical transcriptionist's time is less costly for the hospital than the doctor's time, and the medical transcriptionist is typically much more familiar with the computerized record-keeping systems than the doctor is, so this system offers a significant overall cost saving to the hospital.

The information dictated by the doctor often includes sensitive or confidential information, such as patient name, age, visit dates, medical record numbers, account numbers, referring physicians, consulting physicians, and other provider names and addresses, for example. Furthermore, recent federal regulations under the Health Insurance Portability and Accountability Act (HIPAA) increase the importance of maintaining the confidentiality of patient information. For example, HIPAA describes data called "Protected Health Information (PHI)". Protected Health Information includes medical records data in which the patient is identified. As a result of this Act, many security measures are being created to protect this data.

SUMMARY OF THE INVENTION

Embodiments of the invention may provide security that is useful for medical records documents that include patient identification material. A mechanism may be provided that permits documents to be separated from the patient identification during transmission. Thus, an interceptor of a document during transmission will preferably not have enough information to identify the patient to which the document refers. Even if a document and its patient identification information are both intercepted, determining that the two portions of information belong with each other may be difficult. Security may be further enhanced by separating the patient identifying material from the text of the document.

In general, in an aspect, the invention provides a computer program product for use with dictated medical patient information, the computer program product residing on a computer-readable medium and comprising computer-readable instructions for causing a computer to analyze the dictated information, identify likely confidential information in the dictated medical patient information, and treat the likely confidential information disparately from likely non-confidential information in the dictated medical patient information.

Embodiments of the invention may include one or more of the following features. The computer program can be configured to cause the computer to restrict access to the likely confidential information. The instructions for causing the computer to treat the likely confidential information disparately from likely non-confidential information can cause the computer to store the likely confidential information and the likely non-confidential information such that which information is the likely confidential information is discernable. The instructions for causing the computer to treat the likely confidential information disparately from likely non-confidential information can also cause the computer to store a confidential indication in association with the likely-confidential information. The instructions for causing the computer to treat the likely confidential information disparately from likely non-confidential information can further cause the computer to transmit the likely confidential information separately from the likely non-confidential information to a communication network. The instructions for causing the computer to transmit the likely confidential information separately from the likely non-confidential information to a communication network can cause the computer to transmit likely confidential audio dictated information separately from likely non-confidential audio dictated information and to transmit likely confidential transcribed textual information corresponding to the likely confidential audio information separately from likely non-confidential transcribed textual information corresponding to the likely non-confidential audio dictated information.

Embodiments of the invention may further include one or more of the following features. The instructions for causing the computer to identify likely confidential information in the dictated medical patient information can cause the computer to identify particular phrases, containing at least one word, as the likely confidential information. The instructions for causing the computer to identify likely confidential information in the dictated medical patient information can further cause the computer to identify a boundary between a body of a transcribed document associated with the dictated information and at least one of a header and a footer of the transcribed document. The instructions for causing the computer to identify the boundary can further cause the computer to apply a statistical trigger model to the dictated information. The instructions for causing the computer to identify the boundary can also cause the computer to search for trigger phrases, of at least one word, associated with the boundary and compare boundary likelihoods associated with found trigger phrases. The instructions for causing the computer to identify the boundary can cause the computer to determine boundary likelihoods associated with the found trigger phrases by analyzing positions of the found trigger phrases in the dictated information relative to a beginning or an end of the dictated information.

In general, in another aspect, the invention provides a computer program product for use with text transcribed from audio information, the computer program product residing on a computer-readable medium and comprising computer-readable instructions for causing a computer to differentiate between a first portion and a second portion of the text, display the first portion of the text transcribed from audio information, inhibit the second portion of the text from being displayed, and display an indication that the second portion of the text exists.

Embodiments of the invention may include one or more of the following features. The indication that the second portion of the text exists can be a box. The box can be of a fixed size regardless of an amount of text contained in the second portion of the text. The indication that the second portion of the text exists can be an audible indicator. The instructions can be configured to cause the computer to display the indication in a location within the text using a token-alignment file that associates portions of the audio information with portions of the text.

Embodiments of the invention may further include one or more of the following features. The computer product may further include instructions for displaying the second portion of the text in response to a second-portion request for display of the second portion, distinct from a text request for display of the transcribed text. The computer product can include instructions for causing the computer to display the second portion of the text in response to provision of authorization information. Further, the computer product can include instructions for causing the computer to securely store the second portion of the text.

In general, in another aspect, the invention provides a method of processing text transcribed from an audio file regarding a patient, the method comprising displaying a portion of the transcribed text containing non-confidential patient information on a monitor, playing portions of an audio file associated with the transcribed text, and inhibiting a portion of the transcribed text containing confidential patient information from being displayed on the monitor.

Embodiments of the invention can include one or more of the following features. The inhibiting can comprise displaying an indication on the monitor that confidential information is being concealed. The indication can be disposed at a location within the transcribed text corresponding to where the confidential information belongs in the text. The indication can comprise a shaded box. The box can be of a fixed size regardless of an amount of confidential information being concealed. The indication can be an alias for the confidential information. The method can further comprise displaying the confidential information in response to a request to display the confidential information that is distinct from an initial request to display the transcribed text.

In general, in another aspect, the invention provides a method of processing a medical patient dictation, the method comprising analyzing the dictated information, identifying likely confidential information in the dictated medical patient information, and treating the likely confidential information disparately from likely non-confidential information in the dictated medical patient information.

Embodiments of the invention can include one or more of the following features. The method may further comprise labeling a portion of the dictated information to distinguish the likely confidential information from the likely non-confidential information. The method may further comprise inhibiting access to the likely confidential information. The method may also comprise transmitting the likely confidential information and the likely non-confidential information separately over a communication network. The method still further may comprise identifying a boundary between a body of a transcribed document associated with the medical patient dictation and at least one of a header and a footer of the transcribed document. Identifying the boundary can comprise applying a statistical trigger model to the medical patient dictation. Applying the statistical trigger model may comprise searching for trigger phrases, of at least one word, associated with the boundary and comparing boundary likelihoods associated with found trigger phrases.

Aspects of the invention may include one or more of the following capabilities. Confidential information is removed or concealed from the body of a medical record document. The confidential information is accessible to authorized users by listening to audio associated with a medical record document, or by accessing a secure database. Separate audio files having various levels of confidential information can be transmitted and/or stored separately from non-confidential information. Separate text files having various levels of confidential information can be transmitted and/or stored separately from non-confidential transcribed information. The confidential information is secured by associating it with a medical record document via a unique identifier. Medical records information contained in clinician audio dictations are de-identified from the resulting transcriptions. Transcribed information can be added or changed at a transcription device without revealing the confidential information. The cost of medical transcription is reduced. Information associated with a patient's identity can be inhibited from being paired with information of a patient's medical exam by an interceptor of information transmitted over a public network.

These and other capabilities of the invention, along with the invention itself, will be more fully understood after a review of the following figures, detailed description, and claims.

DETAILED DESCRIPTION OF PREFERRED EMBODIMENTS

Embodiments of the invention can provide a secure database for the storage of confidential information related to documents associated with a digital audio signal of speech to be transcribed. Confidential information can be removed from the body of a medical records document. Authorized users access the confidential information by listening to the audio associated with the document. Confidential information is stored separately in textual form in a medical records database, and associated with a medical record document. Confidential information is concealed from view in a text document being edited. The private information is accessible to authorized persons via a login or a password. Other embodiments are within the scope of the disclosure.

Figure 1:
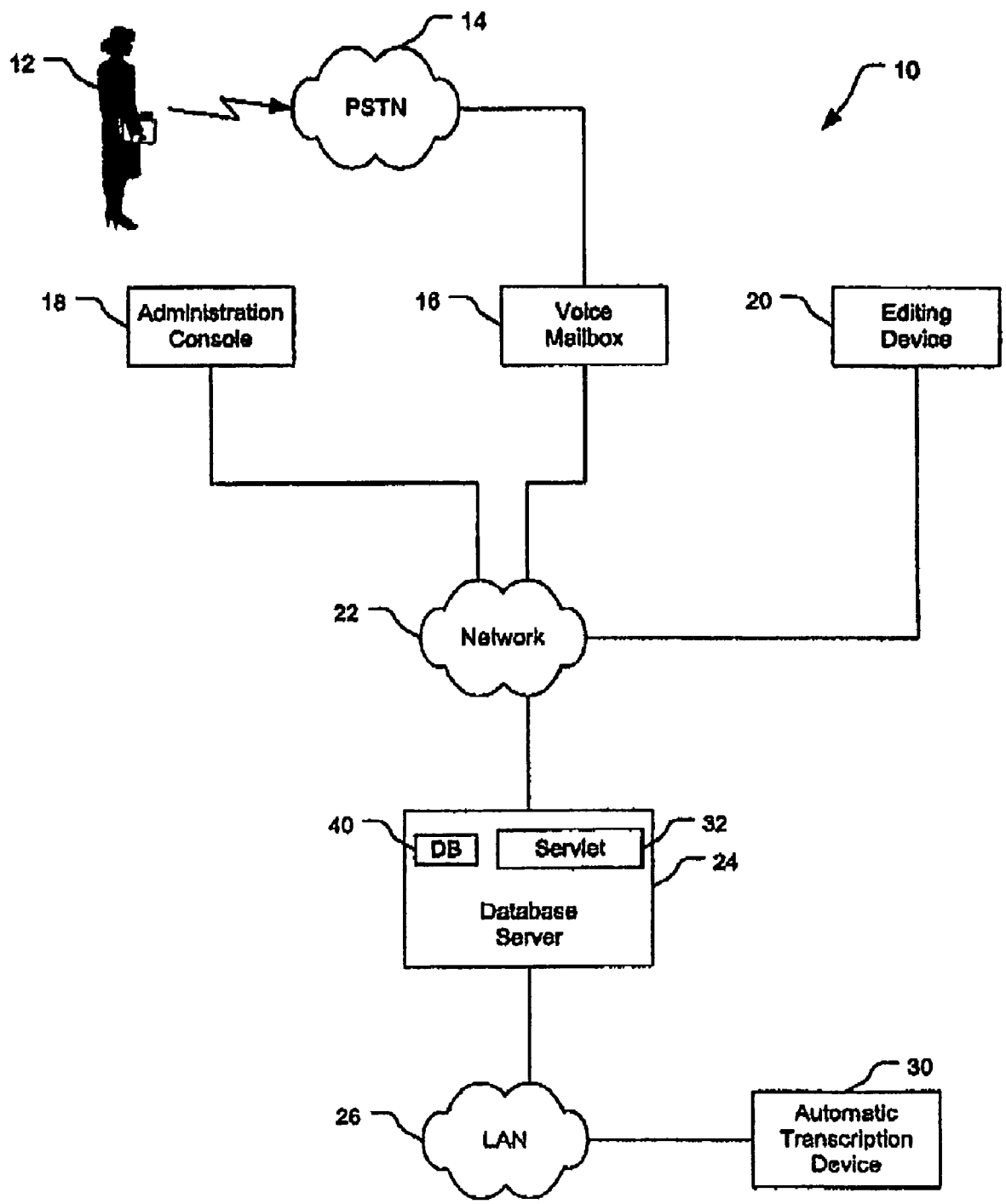
FIG. 1 is a simplified diagram of a system for transcribing dictations and editing corresponding transcriptions.

Referring to FIG. 1, a system 10 for transcribing audio and editing transcribed audio includes a speaker/person 12, a communications network 14, a voice mailbox system 16, an administrative console 18, an editing device 20, a communications network 22, a database server 24, a communications network 26, and an automatic transcription device 30. Here, the network 14 is preferably a public switched telephone network (PSTN) although other networks, including packet-switched networks could be used, e.g., if the speaker 12 uses an Internet phone for dictation. The network 22 is preferably a packet-switched network such as the global packet-switched network known as the Internet. The network 26 is preferably a packet-switched, local area network (LAN). Other types of networks may be used, however, for the networks 14, 22, 26, or any or all of the networks 14, 22, 26 may be eliminated, e.g., if items shown in FIG. 1 are combined or eliminated.

Preferably, the voice mailbox system 16, the administrative console 18, and the editing device 20 are situated "off site" from the database server 24 and the automatic transcription device 30. These systems/devices 16, 18, 20, however, could be located "on site," and communications between them may take place, e.g., over a local area network. Similarly, it is possible to locate the automatic transcription device 30 off-site, and have the device 30 communicate with the database server 24 over the network 22.

The network 14 is configured to convey dictation from the speaker 12 to the voice mailbox system 16. Preferably, the speaker 12 dictates into an audio transducer such as a telephone, and the transduced audio is transmitted over the telephone network 14 into the voice mailbox system 16, such as the Intelliscript™ product made by eScription™ of Needham, Mass. The speaker 12 may, however, use means other than a standard telephone for creating a digital audio file for each dictation. For example, the speaker 12 may dictate into a handheld PDA device that includes its own digitization mechanism for storing the audio file. Or, the speaker 12 may use a standard "dictation station," such as those provided by many vendors. Still other devices may be used by the speaker 12 for dictating, and possibly digitizing the dictation, and sending it to the voice mailbox system 16.

The voice mailbox system 16 is configured to digitize audio from the speaker 12 to produce a digital audio file of the dictation. For example, the system 16 may use the Intelliscript™ product made by eScription.

The voice mailbox system 16 is further configured to prompt the speaker 12 to enter an identification code and a worktype code. The speaker 12 can enter the codes, e.g., by pressing buttons on a telephone to send DTMF tones, or by speaking the codes into the telephone. The system 16 may provide speech recognition to convert the spoken codes into a digital identification code and a digital worktype code. The mailbox system 16 is further configured to store the identifying code and the worktype code in association with the dictation. The system 16 preferably prompts the speaker 12 to provide the worktype code at least for each dictation related to the medical field. The worktype code designates a category of work to which the dictation pertains, e.g., for medical applications this could include Office Note, Consultation, Operative Note, Discharge Summary, Radiology report, etc. The worktype code may be used to refine speed settings, such that settings may be specific not only to speaker-transcriptionist pairings, but further to worktype of dictations provided by the speaker, and/or to other parameters or indicia. The following discussion, however, focuses on using only speaker-transcriptionist pairings.

The voice mailbox system 16 is further configured to transmit the digital audio file and speaker identification code over the network 22 to the database server 24 for storage. This transmission is accomplished by the system 16 product using standard network transmission protocols communicating with the database server 24.

The database server 24 is configured to store the incoming data from the voice mailbox system 16, as well as from other sources. For example, information such as patient Medical Record Number (MRN), date of dictation, date of encounter, account number, and other information can originate from the voice mailbox system 16, from a hospital billing system, or from another source. The database server 24 may include the EditScript Server™ database product from eScription. Software of the database server is configured to produce a database record for the dictation, including a file pointer to the digital audio data, and a field containing the identification code for the speaker 12. If the audio and identifying data are stored on a PDA, the PDA may be connected to a computer running the HandiScript™ software product made by eScription that will perform the data transfer and communication with the database server 24 to enable a database record to be produced for the dictation.

Preferably, all communication with the database server 24 is intermediated by a "servlet" application 32 that includes an in-memory cached representation of recent database entries. The servlet 32 is configured to service requests from the voice mailbox system 16, the automatic transcription device 30, the editing device 20, and the administrative console 18, reading from the database when the servlet's cache does not contain the required information. The servlet 32 includes a separate software module that helps ensure that the servlet's cache is synchronized with the contents of the database. This helps allow the database to be off-loaded of much of the real-time data-communication and to grow to be much larger than otherwise possible. For simplicity, however, the below discussion does not refer to the servlet, but all database access activities may be realized using the servlet application 32 as an intermediary.

The automatic transcription device 30 may access the database 40 in the database server 24 over the data network 26 for transcribing the stored dictation. The automatic transcription device 30 uses an automatic speech recognition (ASR) device (e.g., software) to produce a draft transcription for the dictation. An example of ASR technology is the AutoScript™ product made by eScription that also uses the speaker and, optionally, worktype identifying information to access speaker and speaker-worktype dependent ASR models with which to perform the transcription.

The device 30 transmits the draft transcription over the data network 26 to the database server 24 for storage in the database and to be accessed, along with the digital audio file, by the editing device 20.

The device 30 is further configured to affect the presentation of the draft transcription. The device 30, as part of speech recognition or as part of post-processing after speech recognition, can add or change items affecting document presentation such as formats, abbreviations, and other text features. The device 28 includes a speech recognizer and may also include a post-processor for performing operations in addition to the speech recognition, although the speech recognizer itself may perform some or all of these additional functions.

Automatic speech recognition (ASR) models in the device 30 used to produce draft transcriptions include different types of grammars for recognizing the speaker's dictation. The grammars can be, for example, generic, specific, or intermediate. Generic grammars are designed to recognize speech from a random speaker. Specific grammars are designed/adapted for a particular speaker, either being designed from scratch for the speaker 12 or having been adapted from a more general grammar in response to previous dictations and edited transcriptions. An example of an intermediate grammar is a grammar designed not for a particular speaker, but for speakers that are likely to follow a particular pattern. For example, doctors from a particular institution may be instructed to dictate patient records with a particular format, and the grammar can be designed to improve recognition based on knowledge of expected phrases and/or organization of the patient record.

The automatic transcription device 30 is further configured to identify confidential portions of dictations, including particular data, header regions, and footer regions. Confidential/private patient information includes, e.g., patient name, medical record number, and/or other information from which a patient's identity may be discerned, at least to reasonable (or unacceptable) degree of certainty. The ASR models can be used to identify particular data, such as portions of the dictation that includes the provider name, patient name, patient names spelled out, date of encounter, worktype and/or Medical Record Number (MRN). The device 30 also preferably is able to identify header and footer portions of a dictation as these introductory and closing portions often contain confidential information. The device 30 can analyze the text for the manner in which the speaker begins the dictation. For example, the device 30 may include a grammar such as, "This is Dr. <PROVIDER NAME> dictating an office note on <PATIENT NAME>, medical record number <MRN>. Date of visit is <DATE OF ENCOUNTER>". The device 30 can additionally analyze the text for the manner in which a speaker 12 begins the body of a dictation, which indicates the completion of the header. For example, the device 30 may include a grammar such as, "CHIEF COMPLAINT: Mr. <PATIENT_LAST_NAME> comes in today complaining of chest pain." The device 30 may also include a grammar related to the manner in which a speaker 12 dictates the end of a note, or footer. For example, the device 30 may include a grammar such as, "This is <PROVIDER NAME>. Please send a copy to <CONTACT1> and <CONTACT2>, as well as to my office."

Preferably, the device 30 uses the grammars to identify the location of the header and footer in a dictation. These grammars provide trigger words or phrases that indicate the boundary from the header to the body of the dictation or from the body of the dictation to the footer. Examples of additional end-of-header (i.e. beginning-of-body) trigger phrases include: "The patient is a", followed by an age; "The patient comes in today complaining of . . . "; "history". Examples of footer (i.e. end-of-body) trigger phrases include: "That's all"; "Please send a copy of this to . . . ". In many cases, these triggers by themselves will be sufficient to reliably identify the end of the header and beginning of the footer. These phrases may, however, be supplemented by a statistical trigger model to help identify the boundaries. The model is statistical in that it determines the likelihood of one or more locations being a header/body or body/footer transition, and uses the most likely location as the actual location of the transition. A statistical trigger model can be used alone, or can be combined with a duration model, such as a specified number of words, for the header, body, and footer in order to resolve ambiguities in determining whether particular grammar is a part of the header or the footer. For example, a statistical analysis may include that the phrase "Please send a copy to . . . " has a 90% probability of being a boundary phrase when it occurs within the final thirty words of a dictation. The statistical trigger model may be constrained by the structure of the document, for example, requiring that the footer follows the body, which follows the header.

The header and footer region of the dictation can alternatively be identified by the transcription device 30 in one of the following ways. The header and footer may be identified by using an instance of a listened-to/transcribed header/footer to form the grammar which is used to remove the header/footer from subsequent dictations. A catalog of grammars from a database of providers may be employed to identify headers/footers. The grammars can be scored to determine likely instances of headers/footers in different grammars. A generalized search for words associated with tags in the token-alignment file, discussed below, can be conducted, and may be narrowed using the current date or medical record numbers.

In the event that speech recognition errors occur, a) known or common errors from speech recognition can be explicitly included; b) "wild-cards" that model words which are known to cause recognition errors can be utilized. For example, instead of "the patient comes in today complaining of", the grammar might be "* patient comes * complaining *", since the non-wildcarded words are known to be reliably recognized. The identified confidential information, including header and footer information, are stored separately and treated differently than non-confidential information for the editing process discussed below. Portions of the dictation that include confidential information can be stored separately from non-confidential information in the database 40. For example, the database 40 may include multiple databases, and the confidential information may be stored in a database separate from a database in which non-confidential information is stored. Confidential information can be stored in the same database, but in a separate portion (e.g., a separate file), as non-confidential information. The confidential information is stored separately in that access to the confidential information is inhibited/restricted such that a user that has access to non-confidential information in the database 40 does not necessarily have access to the confidential information. For example, access to the confidential information may require a password or other security measure. Further, the confidential information that appears in the body of the dictation document is tagged, e.g., to help inhibit access to the confidential information even if it is not contained in the header or footer. Additional security can include encrypting the data before sending the data to the user terminal for the editing process, or encrypting the data while the data is en route to the user terminal.

The transcription device 30 is further configured to produce a token-alignment file that synchronizes the audio with the corresponding text. This file comprises a set of token records, with each record preferably containing a token, a begin index, and an end index. The token comprises a character or a sequence of characters that are to appear on the screen during a word-processing session, or one or more sounds that may or may not appear as text on a screen. A begin index comprises an array reference into the audio file corresponding to the place in the audio file where the corresponding token begins. The end index comprises an array reference into the digital audio file corresponding to the point in the audio file where the corresponding token ends. As an alternative, the end index may not exist separately, with it being assumed that the starting point of the next token (the next begin index) is also the ending point of the previous token. The transcription device 30 can store the token-alignment file in the database 40.

The token-alignment file may contain further information, such as a display indicator and/or a playback indicator. The display indicator's value indicates whether the corresponding token is to be displayed, e.g., on a computer monitor, while the transcription is being edited. Using non-displayed tokens can help facilitate editing of the transcription while maintaining synchronization between on-screen tokens and the digital audio file. For example, a speaker may use an alias, e.g., for a heading, and standard heading (e.g., Physical Examination) may be displayed while the words actually spoken by the speaker (e.g., "On exam today") are audibly played but not displayed as text (hidden). The playback indicator's value indicates whether the corresponding token has audio associated with the token. Using the playback indicator can also help facilitate editing the transcription while maintaining synchronization between on-screen tokens and the digital audio file. The playback indicator's value may be adjusted dynamically during audio playback, e.g., by input from the transcriptionist. The adjustment may, e.g., cause audio associated with corresponding tokens (e.g., hesitation words) to be skipped partially or entirely, that may help increase the transcriptionist's productivity.

The tokens stored in the token-alignment file may or may not correspond to words. Instead, a token may represent one or more characters that appear on a display during editing of the transcription, or sounds that occur in the audio file. Thus, the written transcription may have a different form and/or format than the exact words that were spoken by the person 12. For example, a token may represent conventional words such as "the," "patient," or "esophagogastroduodenoscopy," multiple words, partial words, abbreviations or acronyms, numbers, dates, sounds (e.g., a cough, a yawn, a bell), absence of sound (silence), etc. For example, the speaker 12 may say "USA" and the automatic transcription device 30 may interpret and expand this into "United States of America." In this example, the token is "United States of America" and the begin index would point to the beginning of the audio signal for "USA" and, if the token-alignment file uses end indexes, the end index would point to the end of the audio signal "USA." As another example, the speaker 12 might say "April 2 of last year," and the text might appear on the display as "04/02/2003." The tokens, however, can synchronize the text "04/02/2003" with the audio of "April 2 of last year." As another example, the speaker 12 might say "miles per hour" while the text is displayed as "MPH." Using the tokens, the speech recognizer 30, or a post-processor in or separate from the device 30, may alter, expand, contract, and/or format the spoken words when converting to text without losing the audio synchronization. Tokens preferably have variable lengths, with different tokens having different lengths.

The token-alignment file provides an environment with many features. Items may appear on a screen but not have any audio signal associated with them (e.g., implicit titles and headings). Items may have audio associated with them and may appear on the screen but may not appear as words (e.g., numeric tokens such as "120/88"). Items may have audio associated with them, appear on the screen, and appear as words contained in the audio (e.g., "the patient showed delayed recovery"). Multiple words may appear on the screen corresponding to audio that is an abbreviated form of what appears on the screen (e.g., "United States of America" may be displayed corresponding to audio of "USA"). Items may have audio associated with them but not have corresponding symbols appear on the screen (e.g., a cough, an ending salutation such as "that's all," commands or instructions to the transcriptionist such as "start a new paragraph," etc.).

In addition, in the token-alignment file, XML tags, such as <Header>, </Header> and <Footer>, </Footer> are included as zero-duration, non-playable, non-displayable records. Tags are also added around other data contained in the headers and footers. For example, tags can be added to identify <MRN>, <DATE OF ENCOUNTER>, and <CONTACTS>. In the body of the dictation, tags are added around recognized information, including but not limited to <PATIENT NAME>, <PROVIDER NAME>, and <CONTACTS>. The tags allow identification of words in the dictation that contain specific information. The specified words can be manipulated due to the tag assigned to the words. For example, the words having specified tags associated with private/confidential information can be blocked from view in a transcribed document. At the time of editing, tagged words can be obfuscated. For example, <PATIENT NAME> can be changed to "the patient" or to "Mr. ???" for instances of its occurrence throughout the transcribed document to protect the identity of the patient.

Referring further to FIG. 1, the editing device 20 is configured to be used by a transcriptionist to access and edit the draft transcription stored in the database of the database server 24. The editing device 20 includes a computer (e.g., display, keyboard, mouse, monitor, memory, and a processor, etc.), an attached foot-pedal, and appropriate software such as the EditScript™ software product made by eScription. The transcriptionist can log onto the database server 24 with a password. The transcriptionist can request a dictation job by, e.g., clicking on an on-screen icon. The request is serviced by the database server 24, which finds the dictation for the transcriptionist, and transmits the corresponding header, footer, and body audio files and the draft transcription text files. The transcriptionist edits the draft using the editing device 20 and sends the edited transcript back to the database server 24. For example, to end the editing the transcriptionist can click on an on-screen icon button to instruct the editing device 20 to send the final edited document to the database server 24 via the network 22, along with a unique identifier for the transcriptionist. With the data sent from the editing device 20, the database in the server 24 contains, for each dictation: a speaker identifier, a transcriptionist identifier, a file pointer to the digital audio signal, and a file pointer to the edited text document.

The edited text document can be transmitted directly to a customer's medical record system or accessed over the data network 22 from the database by the administrative console 18. The console 18 may include an administrative console software product such as Emon™ made by eScription.

Figure 2:
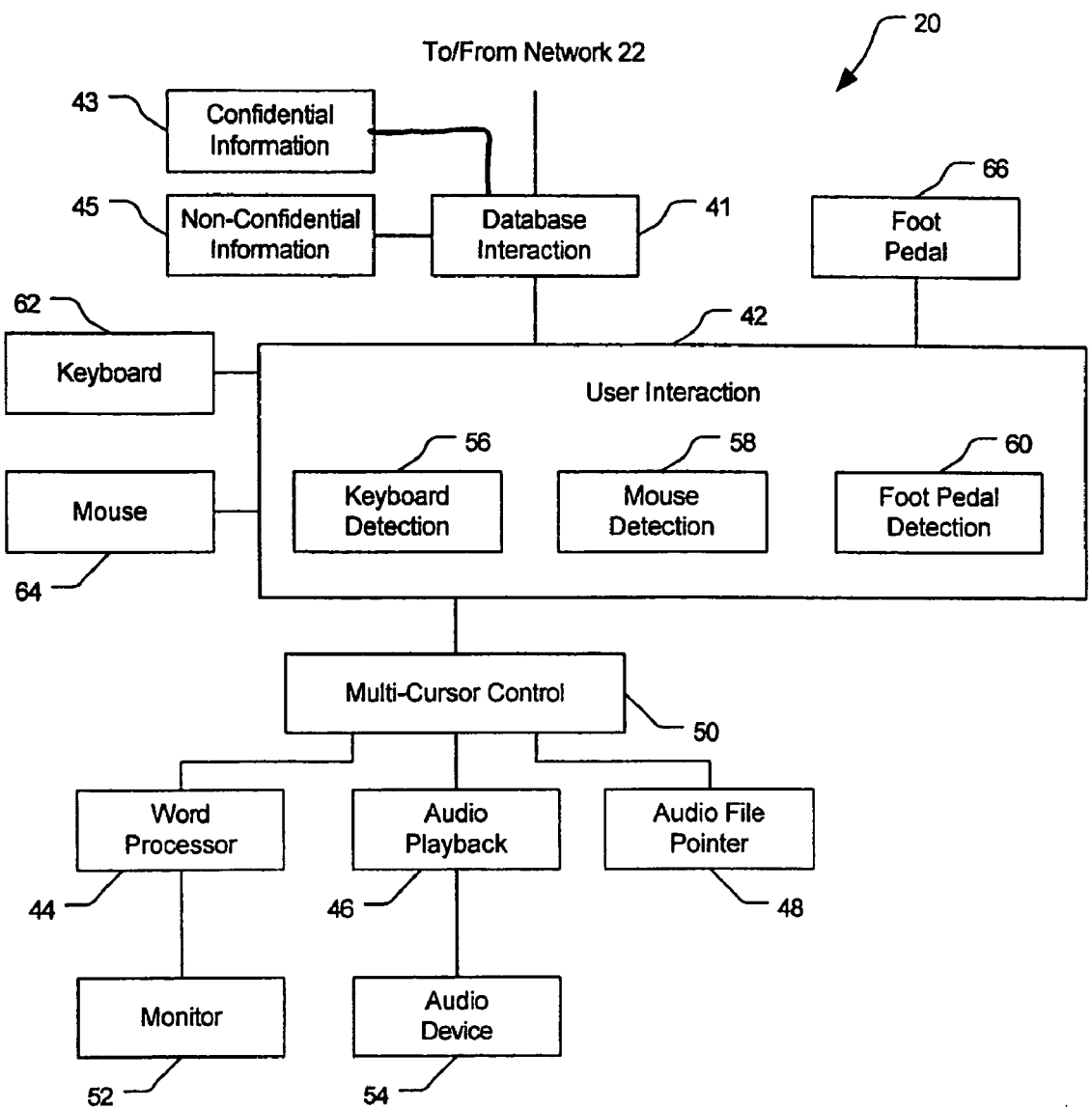
FIG. 2 is a simplified block diagram of an editing device of the system shown in FIG. 1.

Referring to FIG. 2, components of the editing device 20, e.g., a computer, include a database interaction module 41, a user interface 42, non-confidential information storage 43, confidential information storage 45, a word processor module 44, an audio playback module 46, an audio file pointer 48, a cursor module 50, a monitor 52, and an audio device 54. A computer implementing portions of the editing device 20 includes a processor and memory that stores appropriate computer-readable, computer-executable software code instructions that can cause the processor to execute appropriate instructions for performing functions described. The monitor 52 and audio device 54, e.g., speakers, are physical components while the other components shown in FIG. 2 are functional components that may be implemented with software, hardware, etc., or combinations thereof. The audio playback device 46, such as a SoundBlaster® card, is attached to the audio output transducer 54 such as speakers or headphones. The transcriptionist can use the audio device 54 (e.g., headphones or a speaker) to listen to audio and can view the monitor 52 to see the corresponding text. The transcriptionist can use the foot pedal 66, the keyboard 62, and/or the mouse 64 to control the audio playback. The database interaction, audio playback, and editing of the draft transcription is accomplished by means of the appropriate software such as the EditScript Client™ software product made by eScription. The body of dictation files 43 and the header/footer data files are sent to the user interface from the database. The editing software is loaded on the editing device computer 20 and configured appropriately for interaction with other components of the editing device 20. The editing software can use a standard word processing software library, such as that provided with Microsoft Word®, in order to load, edit and save documents corresponding to each dictation.

The editing software includes the database interaction module 41, the user interface module 42, the word processing module 44, the audio playback module 46, the audio file pointer adjustment module 48 and the multi-cursor control module 50. The interaction module 41 regulates communications between database server 24 and the editing device 20 via the network 22. The control module 50 regulates the interaction between the interface module 42 and the word processors 44, the audio playback modules 46, and the audio file pointer 48. The control module 50 regulates the flow of actions relating to processing of a transcription, including playing audio and providing cursors in the transcribed text. The user interface module 42 controls the activity of the other modules and includes keyboard detection 56, mouse detection 58, and foot pedal detection 60 sub-modules for processing input from a keyboard 62, a mouse 64, and a foot-pedal 66. The foot pedal 66 is a standard transcription foot pedal and is connected to the editing device computer through the computer's serial port. The foot pedal 66 preferably includes a "fast forward" portion and a "rewind" portion.

The transcriptionist is permitted to access dictations downloaded to the user interface module 42 based on provider (or groups of providers) and patient identification. The transcriptionist logs onto the user interface module 42 with a logon name and a password so that dictations assigned to a particular transcriptionist are visible in a work queue. The transcriptionist can request a job from the database by selecting on-screen icon with the mouse 64. The user interface module 42 interprets this mouse click and invokes the database interaction module 41 to request the next job from the database 40. The database server 24 (FIG. 1) responds by transmitting the audio data files, the draft transcription files, and the token-alignment files to the user interaction module 42. The audio for confidential information is preferably transmitted to the device 20 separately from the audio for the non-confidential information. Likewise, the text for confidential information is preferably transmitted to the device 20 separately from the text for the non-confidential information. The confidential information is stored in the confidential information storage 43 separate from the non-confidential information storage 45. The confidential information storage 43 can be access-restricted, e.g., by a password and/or other security feature(s). Also, portions of the confidential information can be restricted from access by a particular user, rather than all of the confidential information. With this downloaded information, the editing software can initialize a word-processing session by loading the draft text into the word processing module 44. Audio information is accessed through function calls of the editing program while the dictation is being edited.

The audio playback module 46 is configured to play the audio file associated with the body of the dictation 43 and the audio associated with the header/footer 45. The transcriptionist accesses the audio files 43 and 45 when prepared for editing. For initial playback, the module 46 plays the audio file sequentially. The playback module 46 can, however, jump to audio corresponding to an indicated portion of the transcription and begin playback from the indicated location. For example, the playback module 46 can request the header audio and begin playback of the header. The location may be indicated by a transcriptionist using appropriate portions of the editing device 20 such as the keyboard 62, or the mouse 64. For playback that starts at an indicated location, the playback module 46 uses the token-alignment file to determine the location in the audio file corresponding to the indicated transcription text. Since many audio playback programs play audio in fixed-sized sections (called "frames"), the audio playback module 46 may convert the indicated begin index to the nearest preceding frame for playback. For example, an audio device 54 may play only frames of 128 bytes in length. In this example, the audio playback module uses the token-alignment file to find the nearest prior starting frame that is a multiple of 128 bytes from the beginning of the audio file. Thus, the starting point for audio playback may not correspond precisely to the selected text in the transcription.

The transcriptionist can review and edit a document by appropriately controlling portions of the editing device 20. The transcriptionist can regulate the playback using the foot pedal 66, and listen to the audio corresponding to the text as played by the playback module 46 and converted to sound by the audio device 54. Further, the transcriptionist can move a cursor to a desired portion of the display of the monitor 52 using the keyboard 62 and/or mouse 64, and can make edits at the location of the cursor using the keyboard 62 and/or mouse 64.

The user interface 42 downloads the text of the document to the word processor 44 according to the editing program, which provides restricted access and display of header/footer data and other confidential information. If the transcriptionist positions the cursor for playback of confidential information, then the transcriptionist can be prompted to enter a password, or otherwise fulfill a security measure (e.g., provide bioinformatic information such as a fingerprint) in order to be provided with the text and/or audio corresponding to the confidential information.

Figure 3:
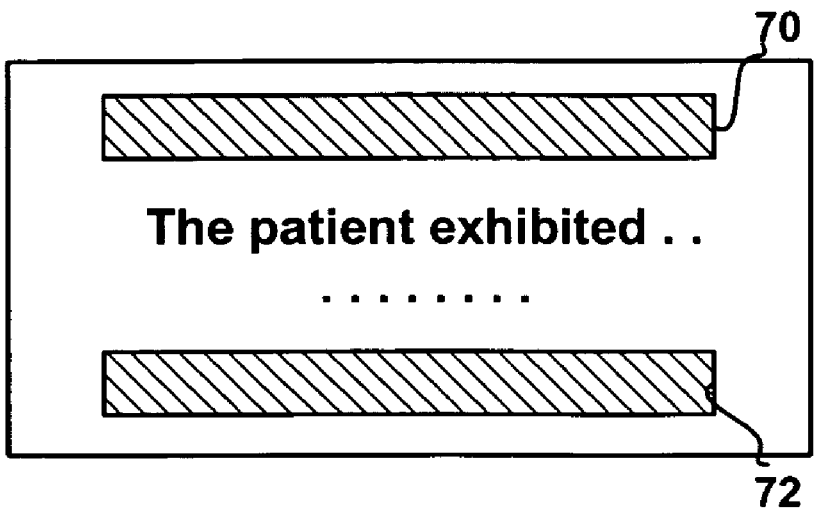
FIG. 3-5 are portions of a transcribed dictation showing concealment of a portion of the text.
Figure 4:
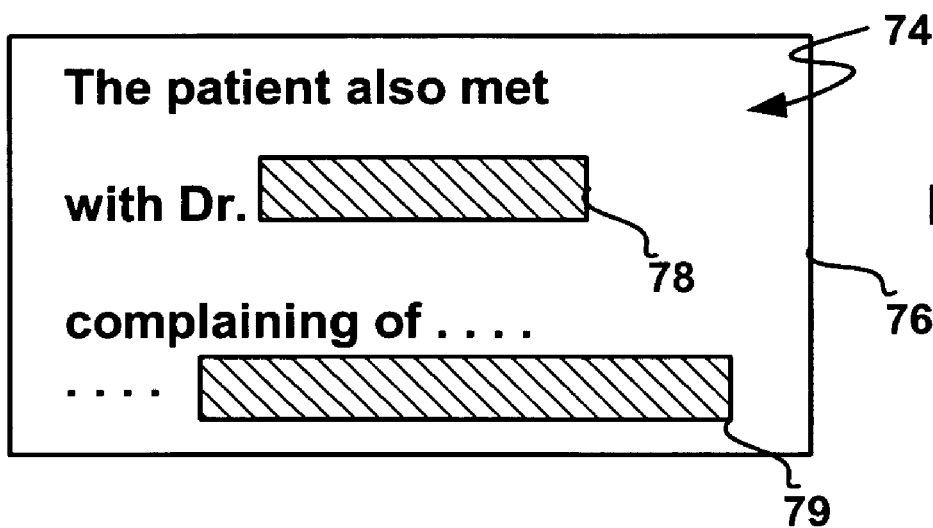
Figure 5:
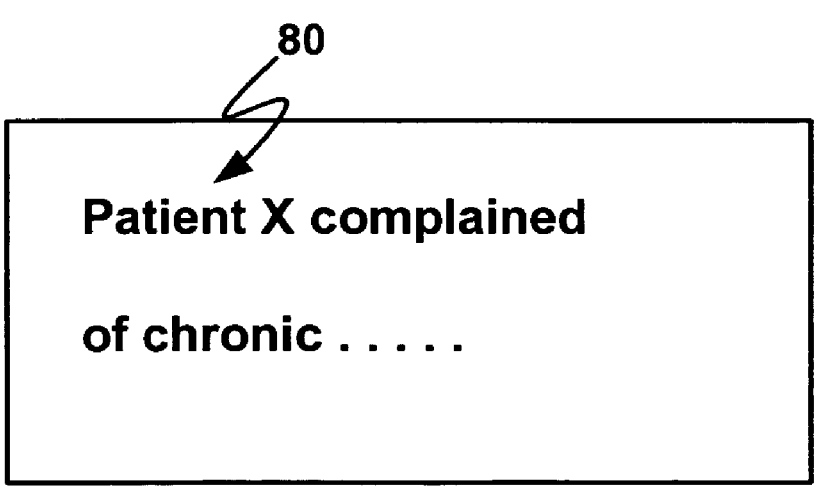

Referring to FIGS. 3-5, confidential information can be obscured/hidden from view absent authorization. As shown in FIG. 3, a header 70 and a footer data 72 appear as gray boxes on the monitor 52. Thus, the confidential data in the header 70 and the footer 72 is not apparent to the user, but is hidden from view. The gray box is preferably of a standard size. As shown in FIG. 4, confidential information contained in a body 74 of a document 76 is hidden with gray boxes 78, 79. The boxes 78, 79 indicate data that have been tagged as confidential, and have been removed from appearing in the body of the text while the document is edited. The boxes 78, 79 are preferably of a standard size to help prevent providing insight into confidential information (e.g., a length of a physician's name). In FIG. 4, the blocked access box 78 indicating a physician's name has been blocked from view, although the name may be presented to the transcriptionist through the audio playback of the dictation. The blocked access boxes 78, 79 allow presentation of the body of a document while concealing confidential information from a viewer. The blocked access boxes 78, 79 may be interactive, allowing an authorized transcriptionist to edit data in or check data that appears in the blocked access block 78 during editing functions. Data entered or reviewed in the boxes 78, 79 may include patient name, provider name, MRN, contacts, etc. Further, as shown in FIG. 4 and FIG. 5, techniques other than gray boxes may be used for concealing confidential information, such as using a generic name 80 ("Patient X") in lieu of actual confidential information. Other generic names include "the patient," "Mr. ??," etc.

A second hot key sequence is used by the transcriptionist to reveal recognized words in the body of the document which have been obfuscated by internal tags. The transcriptionist may use the hot key sequence to call forth and edit the protected language.

While the transcriptionist is editing the document, the user interface module 42 can service hardware interrupts from all three of its sub-modules 56, 58, 60. The transcriptionist can use the foot pedal 66 to indicate that the audio should be "rewound," or "fast-forwarded" to a different time point in the dictation. These foot-pedal presses are serviced as hardware interrupts by the user interaction module 42. Most standard key presses and on-document mouse-clicks are sent to the word processing module 44 to perform the document editing functions indicated and to update the monitor display. Some user interaction, however, may be directed to the audio-playback oriented modules 46, 48, 50, e.g., cursor control, audio position control, and/or volume control. The transcriptionist may indicate that editing is complete by clicking another icon. In response to such an indication, the final text file is sent through the database interaction module 42 to the database server 24.

Figure 6:
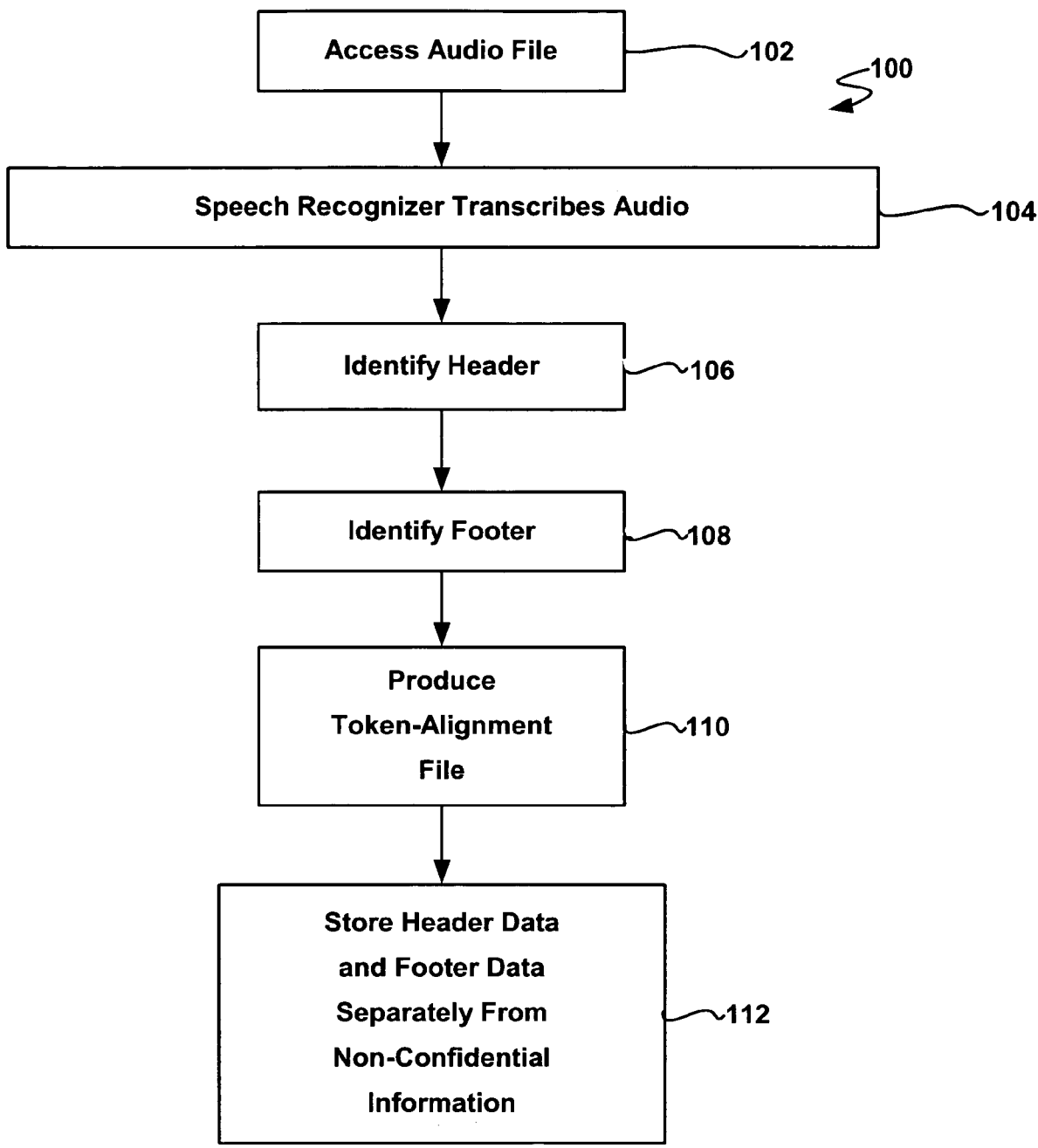
FIG. 6 is a block flow diagram of a process of extracting information from an automatic transcription device.

In operation, referring to FIG. 6, with further reference to FIGS. 1-2, a process 100 for extracting information from a transcription of speech using the system 10 includes the stages shown. The process 100, however, is exemplary only and not limiting. The process 100 may be altered, e.g., by having stages added, removed, or rearranged.

At stage 102, the automatic transcription device 30 seeks to transcribe the audio file, and to extract the header and footer from a dictation audio file stored in the database 40. The automatic transcription device 30 accesses and retrieves the audio file from the database through the LAN 26. The dictation is accompanied by the speaker name (and variants), the patient name (and variants), date information, MRN, as well as other available information.

At stage 104, a speech recognizer of the device 30 analyzes the audio file in accordance with ASR models to produce a draft text document from the audio file. The ASR model includes information on the manner in which physicians dictate to decode word sequence.

At stage 106, the device 30 identifies the header of the dictation using model grammars associated with header language. The identified header is removed from the dictation for separate storage in the database 40. Confidential terms in the header are separately tagged.

At stage 108, the device 30 identifies the footer of the dictation using model grammars associated with footer language. The identified footer is removed from the dictation for separate storage in the database 40. Confidential terms in the header are separately tagged.

At stage 110, the device 30 also produces a corresponding token-alignment file that includes the draft documents and associated portions of the audio file with the transcribed text of the documents. The token-alignment files include XML tags, such as <HEADER></HEADER> and <FOOTER></FOOTER> as meta information for the editing software, described below. The device 30 stores the token-alignment file in the database 40 via the LAN 26.

At stage 112, the header and the footer are stored in the database separate from other portions of the dictation. The header and footer are stored in a secure portion of memory in the server 24. The remainder of the dictation is stored separately from the confidential information, e.g., in a separate file.

Figure 7:
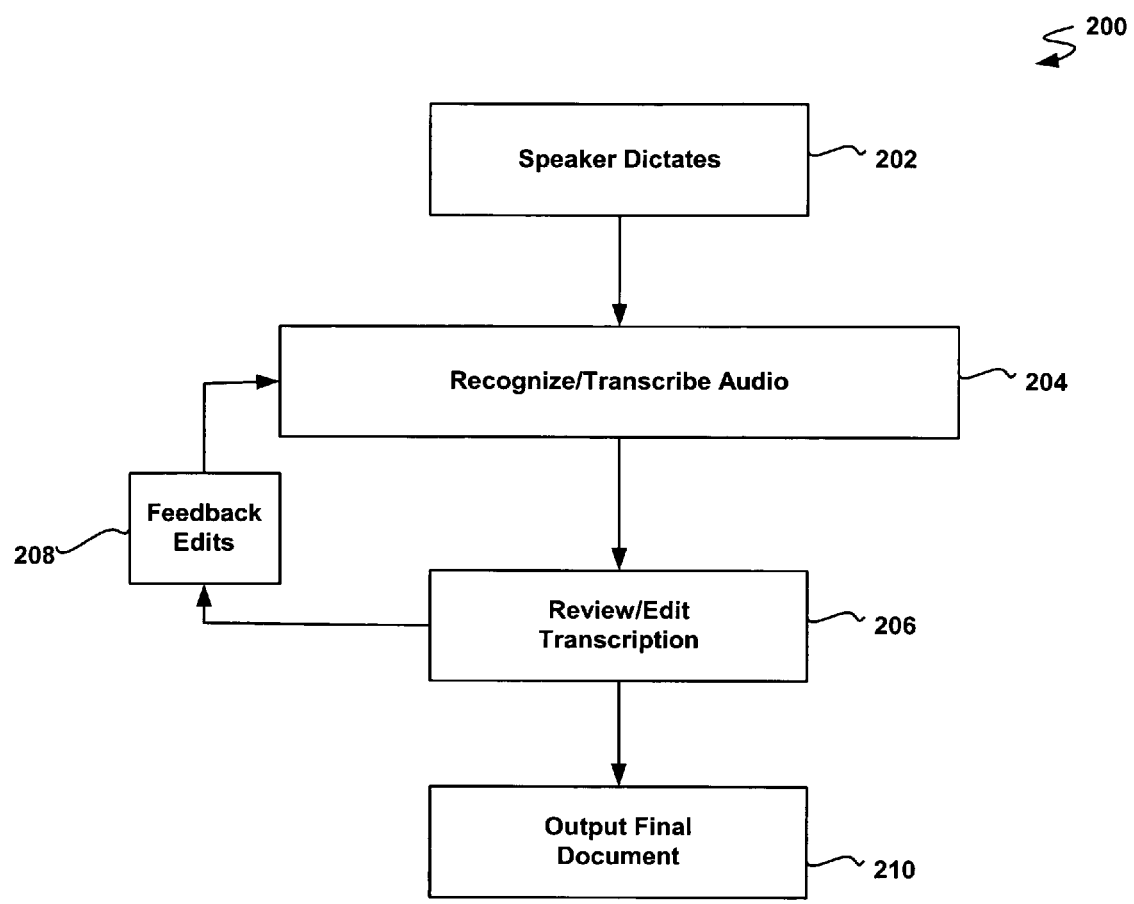
FIG. 7 is a block flow diagram of a process of producing and editing a transcription.

In operation, referring to FIG. 7, with further reference to FIG. 1-6, a process 200 for producing and editing a transcription of speech using the system 10 includes the stages shown. The process 200, however, is exemplary only and not limiting. The process 200 may be altered, e.g., by having stages added, removed, or rearranged.

At stage 202, the speaker 12 dictates desired speech to be converted to text. The speaker can use, e.g., a hand-held device such as a personal digital assistant, to dictate audio that is transmitted over the network 14 to the voice mailbox 16. The audio is stored in the voice mailbox 16 as at least one audio file. The audio file is transmitted over the network 22 to the database server 24 and is stored in the database 40.

At stage 204, the automatic transcription device 30 seeks to transcribe the audio file according to the process 100 in FIG. 6. The automatic transcription device 30 accesses and retrieves the audio file from the database through the LAN 26. The dictation is accompanied by the speaker name (and variants), the patient name (and variants), date information, MRN, as well as other available information.

At stage 206, the transcriptionist reviews and edits the transcribed draft document as appropriate. The transcriptionist uses the editing device 20 to access the database 40 and retrieve the audio file and the token-alignment file that includes the draft text document. The editing of header and footer data is further described below with respect to FIG. 8. The transcriptionist plays the audio file and reviews the corresponding text as highlighted or otherwise indicated by an audio cursor and makes desired edits using, e.g., a text cursor 72. The word processor 44 produces and stores track-changes information in response to edits made by the transcriptionist.

At stage 208, the track-changes information is provided to the automatic transcription device 30 for use in improving the speech models used by the speech recognizer of the device 30 by analyzing the transcribed draft text and what revisions were made by the transcriptionist. The models can be adjusted so that the next time the speech recognizer analyzes speech that was edited by the transcriptionist, the recognizer will transcribe the same or similar audio to the edited text instead of the draft text previously provided. At stage 210, the word processor provides a final, revised text document as edited by the transcriptionist. This final document can be stored in the database 40 and provided via the network 22 to interested parties, e.g., the speaker that dictated the audio file.

Figure 8:
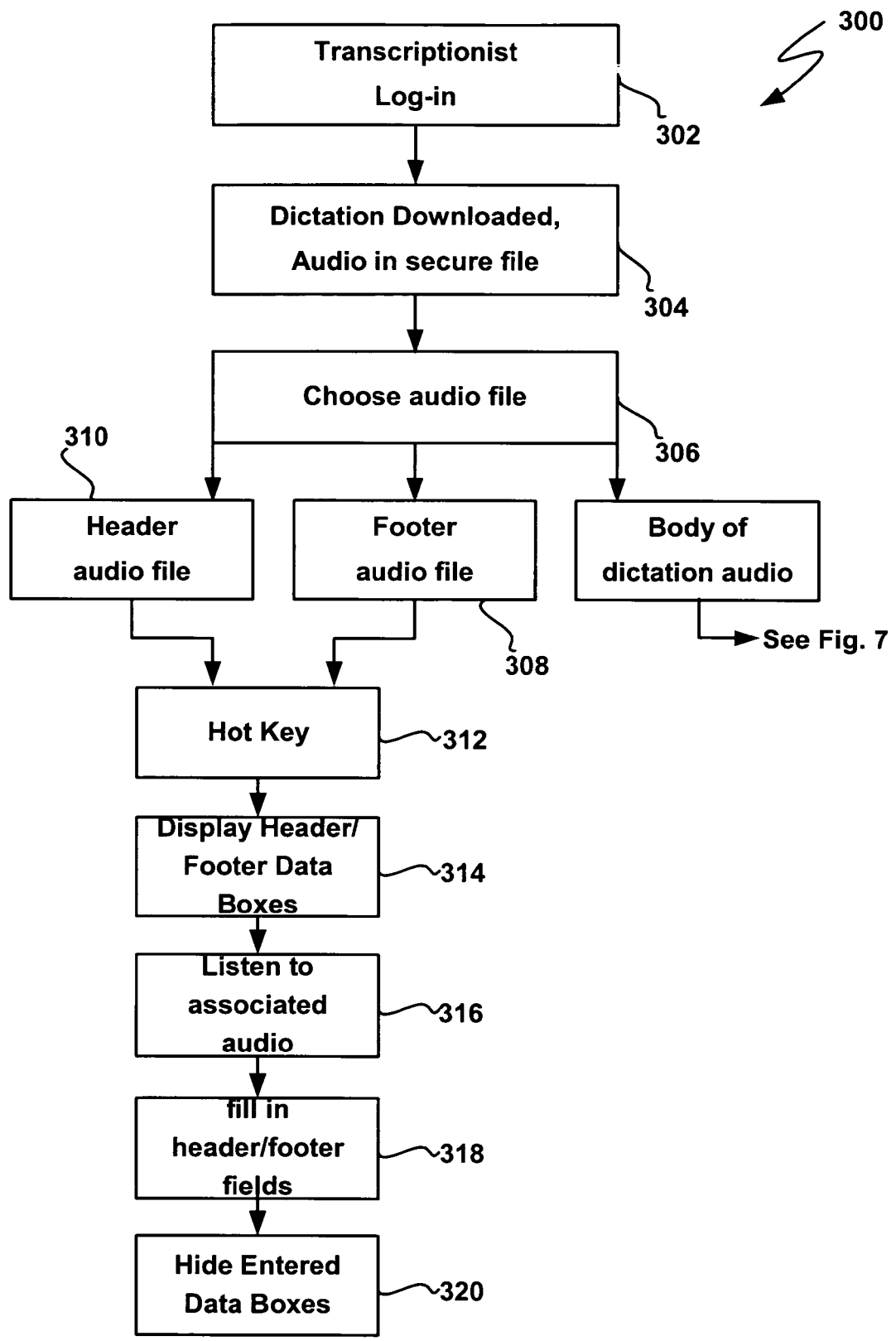
FIG. 8 is a block flow diagram of a process of editing information extracted from an automatic transcription device.

Referring to FIG. 8, with further reference to FIGS. 1-7, a process 300 for editing the header/footer data of the draft transcribed document, continued from stage 206 of FIG. 7, using the editing device 20 includes the stages shown. The process 300, however, is exemplary only and not limiting. The process 300 may be altered, e.g., by having stages added, removed, or rearranged.

At stage 302, the transcriptionist logs in with a user name and password, and dictations assigned to them are shown in the queue. When a dictation is chosen, the audio and document are downloaded, preferably separately, to the transcriptionist's computer. The audio is preferably stored in a secure location. The audio may be separated into more than one file, such as a file for the header, a file for the footer, and a file for the body. Information from the token alignment file is used to find the correct location in the audio file in order to accomplish the audio separation.

In exemplary embodiments, audio separation is employed to additionally alter the audio file to remove patient identification information. For example, the audio might sound a tone in lieu of a spoken patient name is spoken. The audio exchanged for the confidential information may alternatively be an alias for the confidential term, such as a generic name, or other desired sound masking/concealing the actual spoken audio.

When the document is being edited, particular audio files can be accessed. The file-read permissions on the audio files and the document can restrict access to anyone but the transcriptionist who has logged on.

At stage 306, the transcriptionist chooses an audio file associated with either the header, the footer, or the body. If the header or the footer are desired to be edited, the transcriptionist activates a hot key, at stage 312, to call forth the grey boxes 78, 79 so that the boxes appear on the monitor 52. At stage 314, the blocked access boxes 78, 79 are displayed, and at stage 316, the transcriptionist listens to audio associated with the header. A similar procedure would be used for editing other portions of a document containing confidential information. The transcriptionist may be required to enter a password or provide other security information before the grey boxes 78, 79 appear on the monitor.

At stage 318, the header fields are reviewed and/or edited. Data appearing in the grey boxes includes patient name and other confidential data that is reviewed for accuracy. Upon completion of editing, at stage 320, the grey boxes 78, 79 are hidden from view once again. Data entered into the boxes is no longer visible on the monitor 52.

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. In exemplary embodiments of the invention, the header and footer data are identified and separately stored in a database. It is possible that only one of the header and the footer may be identified and separately stored, or both the header and the footer data can be stored, e.g., in a common file separate from the remainder of the document. Storage of the header and the footer may not be separate from the remainder of the document, but transmittal of the header and the footer may be separated from transmittal of the remainder of the document. In an alternative embodiment, the editing program can include a timeout portion which observes whether there has been a break in editing or audio playback for a given amount of time.

What is claimed is:

1. A computer-readable medium encoded with computer executable instructions, the computer executable instructions for use with dictated medical patient information, the computer executable instructions configured to, when executed by at least one computer, cause the at least one computer to:
    transcribe the dictated medical patient information to produce transcribed text;
    analyze the transcribed text transcribed from the dictated medical patient information to identify likely confidential information in the dictated medical patient information; and
    treat the likely confidential information disparately from likely non-confidential information in the dictated medical patient information, wherein at least some of the likely confidential information is related to an identity of a patient associated with the dictated medical patient information, and wherein the instructions for causing the at least one computer to identify likely confidential information in the dictated medical patient information include instructions for causing the at least one computer to identify particular phrases, containing at least one word, as at least part of the likely confidential information.

2. A computer-readable medium encoded with computer executable instructions, the computer executable instructions for use with dictated medical patient information, the computer executable instructions configured to, when executed by at least one computer, cause the at least one computer to:
    transcribe the dictated medical patient information to produce transcribed text;
    analyze the transcribed text transcribed from the dictated medical patient information to identify likely confidential information in the dictated medical patient information; and
    treat the likely confidential information disparately from likely non-confidential information in the dictated medical patient information, wherein at least some of the likely confidential information is related to an identity of a patient associated with the dictated medical patient information, and wherein the instructions for causing the at least one computer to treat the likely confidential information disparately from likely non-confidential information include instructions for causing the at least one computer to transmit the likely confidential information separately from the likely non-confidential information to a communication network.

3. The computer-readable medium program product of claim 2 wherein the likely confidential information is associated with at least one confidential portion of the transcribed text and at least one confidential portion of the dictated medical patient information where the confidential information respectively has been identified, wherein other portions are deemed likely non-confidential portions of the transcribed text and non-confidential portions of the dictated medical patient information, and wherein instructions for causing the at least one computer to transmit the likely confidential information separately from the likely non-confidential information to a communication network include instructions for causing the at least one computer to:
    transmit the at least one confidential portion of the dictated medical patient information separately from likely non-confidential portions of the dictated medical patient information; and
    transmit the at least one confidential portion of the transcribed text separately from likely non-confidential portions of the transcribed text.

4. A computer-readable medium encoded with computer executable instructions, the computer executable instructions for use with dictated medical patient information, the computer executable instructions configured to, when executed by at least one computer, cause the at least one computer to:
 transcribe the dictated medical patient information to produce transcribed text;
 analyze the transcribed text transcribed from the dictated medical patient information to identify likely confidential information in the dictated medical patient information; and
 treat the likely confidential information disparately from likely non-confidential information in the dictated medical patient information, wherein at least some of the likely confidential information is related to an identity of a patient associated with the dictated medical patient information, and wherein the instructions for causing the at least one computer to treat the likely confidential information disparately from likely non-confidential information include instructions for causing the at least one computer to store an indication of confidentiality in association with the likely confidential information.

5. A computer-readable medium encoded with computer executable instructions, the computer executable instructions for use with dictated medical patient information, the computer executable instructions configured to, when executed by at least one computer, cause the at least one computer to:
 transcribe the dictated medical patient information to produce transcribed text;
 analyze the transcribed text transcribed from the dictated medical patient information to identify likely confidential information in the dictated medical patient information; and
 treat the likely confidential information disparately from likely non-confidential information in the dictated medical patient information, wherein at least some of the likely confidential information is related to an identity of a patient associated with the dictated medical patient information, and wherein the instructions for causing the at least one computer to identify likely confidential information in the dictated medical patient information include instructions for causing the at least one computer to identify a boundary between a body of the transcribed text and at least one of a header and a footer of the transcribed text.

6. The computer-readable medium of claim 5 wherein the instructions for causing the at least one computer to identify the boundary includes instructions for causing the at least one computer to apply a statistical trigger model to the dictated medical patient information.

7. The computer-readable medium program of claim 6 wherein the instructions for causing the at least one computer to identify the boundary include instructions for causing the at least one computer to search for trigger phrases, of at least one word, associated with the boundary and compare boundary likelihoods associated with found trigger phrases.

8. The computer-readable medium of claim 7 wherein the instructions for causing the at least one computer to identify the boundary include instructions for causing the at least one computer to determine boundary likelihoods associated with the found trigger phrases by analyzing positions of the found trigger phrases in the dictated medical patient information relative to a beginning or an end of the dictated medical patient information.

9. A computer-readable medium encoded with computer executable instructions, the computer executable instructions for use with text transcribed from audio information, the computer executable instructions configured to, when executed by at least one computer, cause the at least one computer to:
 analyze the text transcribed from audio information to differentiate between a first portion and a second portion of the text transcribed from the audio information, the second portion being differentiated from the first portion, at least in part, by the identification of likely confidential information in the second portion;
 display the first portion of the text transcribed from the audio information;
 inhibit the second portion of the text from being displayed; and
 display an indication that the second portion of the text exists, wherein the instructions for causing the at least one computer to display the first portion include instructions for causing the at least one computer to display the first portion to a transcriber for viewing, and wherein the instructions for causing the at least one computer to display the indication includes instructions for causing the at least one computer to display the indication to the transcriber to indicate that the second portion exists but has been identified as likely confidential and is being inhibited from being displayed.

10. The computer-readable medium of claim 9 wherein the instructions for causing the at least one computer to display the indication includes instructions for causing the at least one computer to display the indication as a box such that the transcriber is aware that likely confidential information exists, but is prevented from directly viewing the likely confidential information.

11. The computer-readable medium of claim 9 further comprising instructions for causing the at least one computer to:
 request authorization information in response to a request to view the second portion, the authorization information indicating that the viewer is authorized to view the second portion, and
 display the second portion of the text in response to provision of the authorization information.

12. The computer-readable medium of claim 11 wherein the instructions for causing the at least one computer to display the authorization information includes instructions for causing the at least one computer to request a viewer provide a password, and to display the second portion when a valid password is provided.

13. A computer-readable medium encoded with computer executable instructions, the computer executable instructions for use with text transcribed from audio information, the computer executable instructions configured to when executed by at least one computer, cause the at least one computer to:
 analyze the text transcribed from audio information to differentiate between a first portion and a second portion of the text transcribed from the audio information, the second portion being differentiated from the first portion, at least in part, by the identification of likely confidential information in the second portion;
 display the first portion of the text transcribed from the audio information;
 inhibit the second portion of the text from being displayed; and
 display an indication that the second portion of the text exists wherein the audio information is dictated medical patient information and at least some of the likely confidential information is related to an identity of a patient associated with the dictated medical patient information.

14. The computer-readable medium of claim 13 wherein the at least some of the likely confidential information related to the identity of the patients includes at least one identity indicator selected from the group consisting of: a patient name, a provider name and a medical record number (MRN), and wherein the instructions for causing the at least one computer to display the indication includes instructions for causing the at least one computer to display an alias in place of the at least one identity indicator.

15. A computer-readable medium encoded with computer executable instructions, the computer executable instructions for use with text transcribed from audio information, the computer executable instructions configured to, when executed by at least one computer, cause the at least one computer to:
    analyze the text transcribed from audio information to differentiate between a first portion and a second portion of the text transcribed from the audio information, the second portion being differentiated from the first portion, at least in part, by the identification of likely confidential information in the second portion;
    display the first portion of the text transcribed from the audio information;
    inhibit the second portion of the text from being displayed; and
    display an indication that the second portion of the text exists, wherein the instructions are configured to provide an alternate sound in place of portions of the audio information associated with the second portion of the text, the alternate sound replacing the audio information associated with the second portion of the text when played to prevent the likely confidential information from being heard.

16. A computer-readable medium encoded with computer executable instructions, the computer executable instructions for use with text transcribed from audio information, the computer executable instructions configured to, when executed by at least one computer, cause the at least one computer to:
    analyze the text transcribed from audio information to differentiate between a first portion and a second portion of the text transcribed from the audio information, the second portion being differentiated from the first portion, at least in part, by the identification of likely confidential information in the second portion;
    display the first portion of the text transcribed from the audio information;
    inhibit the second portion of the text from being displayed; and
    display an indication that the second portion of the text exists, wherein the instructions are configured to cause the at least one computer to display the indication in a location within the text using a token-alignment file that associates portions of the audio information with corresponding portions of the text.

17. A method of processing, using at least one computer, text transcribed from an audio file associated with a patient, the method comprising:
    analyzing the text transcribed from the audio file to identify confidential patient information;
    displaying a portion of the transcribed text containing non-confidential patient information on a monitor;
    playing portions of an audio file associated with the transcribed text containing the non-confidential patient information;
    inhibiting a portion of the transcribed text containing the confidential patient information from being displayed on the monitor; and
    providing an alternate sound in place of the audio information associated with the portion of the text containing confidential patient information, the alternate sound replacing the audio information associated with the portion of the text containing the confidential patient information when played to prevent the confidential patient information from being heard.

18. A method of processing, using at least one computer, text transcribed from an audio file associated with a patient, the method comprising:
    analyzing the text transcribed from the audio file to identify confidential patient information;
    displaying a portion of the transcribed text containing non-confidential patient information on a monitor;
    playing portions of an audio file associated with the transcribed text containing the non-confidential patient information;
    inhibiting a portion of the transcribed text containing the confidential patient information from being displayed on the monitor; and
    requesting authorization information in response to a request to view the confidential patient information that is distinct from an initial request to display the transcribed text wherein displaying of the confidential patient information is inhibited, the authorization information indicating that the viewer is authorized to view the second portion, and displaying the confidential patient information in response to receiving the authorization information.

* * * * *

UNITED STATES PATENT AND TRADEMARK OFFICE
CERTIFICATE OF CORRECTION

PATENT NO. : 7,650,628 B2  Page 1 of 1
APPLICATION NO. : 10/970617
DATED : January 19, 2010
INVENTOR(S) : Zimmerman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 922 days.

Signed and Sealed this

Twenty-third Day of November, 2010

David J. Kappos
*Director of the United States Patent and Trademark Office*